(12) United States Patent
Jin (10) Patent No.: US 12,274,418 B2
(45) Date of Patent: Apr. 15, 2025

(54) MEDICAL INSTRUMENT WITH ANGLE ADJUSTMENT DEVICE

(71) Applicant: SUZHOU FRANKENMAN MEDICAL INSTRUMENTS CO., LTD., Suzhou (CN)

(72) Inventor: Fukang Jin, Suzhou (CN)

(73) Assignee: SUZHOU FRANKENMAN MEDICAL INSTRUMENTS CO., LTD., Suzhou (CN)

( * ) Notice: Subject to any disclaimer, the term of this patent is extended or adjusted under 35 U.S.C. 154(b) by 821 days.

(21) Appl. No.: 17/600,068

(22) PCT Filed: Sep. 9, 2020

(86) PCT No.: PCT/CN2020/114276
§ 371 (c)(1),
(2) Date: Sep. 29, 2021

(87) PCT Pub. No.: WO2021/073319
PCT Pub. Date: Apr. 22, 2021

(65) Prior Publication Data
US 2022/0183539 A1    Jun. 16, 2022

(30) Foreign Application Priority Data
Oct. 14, 2019   (CN) .......................... 201910974609.1

(51) Int. Cl.
*A61B 1/00* (2006.01)
*A61B 1/005* (2006.01)
(Continued)

(52) U.S. Cl.
CPC .......... *A61B 1/0057* (2013.01); *A61B 1/0052* (2013.01); *A61B 1/0055* (2013.01); *A61M 25/0147* (2013.01); *A61M 25/09* (2013.01)

(58) Field of Classification Search
CPC .............. A61M 25/0147; A61M 25/09; A61M 25/09041; A61M 25/06;
(Continued)

(56) References Cited

U.S. PATENT DOCUMENTS

| 2004/0181135 A1* | 9/2004 | Drysen ............. A61M 25/0136 600/374 |
| 2011/0237888 A1 | 9/2011 | Matsushita |

FOREIGN PATENT DOCUMENTS

| CN | 205698858 U | * 4/2015 |
| CN | 106455939 A | 2/2017 |

(Continued)

*Primary Examiner* — Nathan R Price
*Assistant Examiner* — Haden Matthew Ritchie
(74) *Attorney, Agent, or Firm* — SZDC Law PC (57) ABSTRACT

The invention provides a medical instrument with angle adjustment device, including a guidewire output portion, a guidewire guide portion, an adjustment control portion and traction wires. The guidewire output portion is bendable relative to the guidewire guide portion. The guidewire output portion is provided with a guidewire output hole. One end of each traction wire is connected to a proximal end of the guidewire output portion, and the other end of the traction wire is connected to a bending control member of the adjustment control portion. The adjustment control portion controls a bending angle of the guidewire output portion through the traction wire. The ends of the plurality of traction wires are evenly distributed along the guidewire output portion. The positions and quantity of traction wires are set to enable a medical instrument having a distal end with an adjustable bending degree to adjust angles in various directions as required.

8 Claims, 5 Drawing Sheets

(51) Int. Cl.
 *A61M 25/01* (2006.01)
 *A61M 25/09* (2006.01)
(58) Field of Classification Search
 CPC ......... A61M 2025/09116; A61M 2025/09041;
 A61M 2025/09175; A61M 39/1011;
 A61B 1/0057; A61B 1/0052; A61B
 1/0055
 See application file for complete search history.

(56) References Cited

FOREIGN PATENT DOCUMENTS

| | | | |
|---|---|---|---|
| CN | 110575603 | A | 12/2019 |
| CN | 110575604 | A | 12/2019 |
| CN | 110917468 | A | 3/2020 |
| WO | 9414494 | A2 | 7/1994 |

* cited by examiner

MEDICAL INSTRUMENT WITH ANGLE ADJUSTMENT DEVICE

This application is the National Stage Application of PCT/CN2020/114276, filed on Sep. 9, 2020, which claims priority to Chinese Patent Application No. 201910974609.1, filed on Oct. 14, 2019, which is incorporated by reference for all purposes as if fully set forth herein.

FIELD OF THE INVENTION

The present invention relates to a medical device, and in particular, to a medical instrument with angle adjustment device.

DESCRIPTION OF THE RELATED ART

Interventional therapy is a new discipline that integrates radiology and clinical treatment. In the interventional therapy, with the aid of an imaging device, an interventional instrument is guided to a body focus through natural body orifices or very small incisions to perform minimally invasive treatment, so that the interventional instrument can accurately and directly reach a lesion part without causing large wounds. Therefore, the interventional therapy is accurate, safe, and efficient, can be applied to a wide range of indications, and causes few complications, and already becomes a preferred treatment for some diseases. The interventional therapy can be used for many diseases, including nearly all major diseases in systems and organs of the human body.

There are numerous interventional therapy techniques. First, the techniques may include vascular interventional techniques and nonvascular interventional techniques. The nonvascular interventional techniques include various percutaneous biopsies, molding of various nonvascular tracts (including expansion and stenting of strictures such as a urinary tract, a digestive tract, a respiratory tract, and a biliary tract), partial inactivation of solid tumors (percutaneous intratumoral injection, and radiofrequency ablation), cyst and abscess drainage, fistulization (gastrostomy, cystostomy, and the like), minimally invasive cholelithotomy and nephrolithotomy, percutaneous vertebroplasty for bone metastasis or vertebral compression fractures, celiac plexus block for treating chronic pain, and the like.

However, a conventional implant cannot continue when reaching a corner in a human duct, resulting in increased risk in surgery or surgery failure. A directing guidewire may be used as a "path" in a natural duct in a human body, to facilitate the feeding of in vivo medical instruments such as a stent and a balloon in the natural duct in the human body during surgery using interventional therapy. After the directing guidewire enters the elongated natural duct in the human body, a "path" for pressurized expansion is provided for feeding a miniature medical instrument such as a balloon catheter or stent to a narrow lesion, to ensure successful interventional therapy surgery.

Specifically, for the principle and process of feeding a guidewire in the prior art, reference may be made to related patents such as Publication No. CN209004990U, CN208851536U, CN208582446U, and CN106823106A. One of the patents in the prior art is used as an example. The patent application Publication No. CN106823106A provides a guidewire feeding device, including a syringe connecting portion. A front feeding portion and a rear feeding portion are disposed above the syringe connecting portion. A distance is reserved between the front feeding portion and the rear feeding portion to form a booster space. A front feeding channel is provided inside the front feeding portion, and a rear feeding channel is provided inside the rear feeding portion. A front end of the front feeding portion is connected to a first fitting of a three-way Luer taper, and the three-way Luer taper is in communication with the front feeding channel. A gasket is disposed between the first fitting and the front feeding channel. A cross-shaped or "-"-shaped incision is provided in the gasket. A second fitting of the three-way Luer taper is used for connecting a needle. The second fitting, the first fitting, the front feeding channel, and the rear feeding channel are in one straight line. A third fitting of the three-way Luer taper is connected to a connecting tube. A rear end of the rear feeding portion is connected to a guidewire sheath. The guidewire sheath is in communication with the rear feeding channel.

However, in a process of feeding a guidewire, it is usually necessary to adjust an input angle of a guidewire. In an angle adjustment manner in the prior art, an angle in only one single direction can be adjusted. After the angle has been adjusted, an angle of an execution end cannot be adequately fixed.

Therefore, it is necessary to provide a medical instrument that has a guidewire with input angles adjustable in a plurality of directions and can be conveniently fastened.

SUMMARY OF THE INVENTION

In order to overcome the above technical problems, the invention provides the following technical solutions.

A medical instrument with angle adjustment device, including a guidewire output portion, a guidewire guide portion, an adjustment control portion, and traction wires. The guidewire output portion is bendable relative to the guidewire guide portion. The guidewire output portion is provided with a guidewire output hole. One end of each traction wire is connected to a proximal end of the guidewire output portion, and the other end of the traction wire is connected to a bending control member of the adjustment control portion. The adjustment control portion controls a bending angle of the guidewire output portion through the traction wire, that is, a direction and an angle of bending. The number of the traction wires is N. N is a positive integer and is greater than or equal to 3. The ends of the N traction wires are evenly distributed along the guidewire output portion. N is preferably 4. When the number of the traction wires is 2 and the two traction wires are evenly distributed, an angle in only one direction can be adjusted. When three or more traction wires, preferably four traction wires, are provided, angles can be controlled in a plurality of directions, and bending at 360 degrees can be implemented through the coordination of the plurality of traction wires.

Preferably, the guidewire guide portion includes a guide housing, a first flexible bend member is provided at an end of the guide housing, and an end of the first flexible bend member is connected to the guidewire output portion, so that a bending process is smoother and gentler.

Preferably, a traction through hole for the traction wires to pass through and a guidewire feeding through hole for feeding a guidewire are provided inside the guide housing.

Preferably, the adjustment control portion includes a rotary casing, the rotary casing is provided with a channel for a guidewire to pass through, one end of the rotary casing is fixedly connected to the guide housing, and the rotary casing is externally connected to a rotary wheel, so that the guidewire output portion can bend in various directions relative to the guidewire guide portion and can also rotate 360 degrees about a central axis.

Preferably, the other end of the rotary casing is connected to the bending control member by a second flexible bend member.

Preferably, the adjustment control portion further includes a handle, a handle ferrule is provided at an end of the handle, the handle ferrule and a casing of the handle are integrally formed, and a clamping portion of the bending control member is disposed inside the handle ferrule.

Preferably, the adjustment control portion further includes a locking ring and a limit sleeve, the limit sleeve is sleeved on the handle ferrule, an inner surface of the limit sleeve matches an outer surface of the handle ferrule, the locking ring is sleeved on the limit sleeve, and a conical inner surface of the locking ring matches a conical outer surface of the limit sleeve.

Preferably, the handle ferrule is made of an elastic material, and the conical inner surface of the locking ring matches the conical outer surface of the limit sleeve by threaded connection.

Preferably, the guide housing is symmetrically arranged about a central axis, and a distance from the other end of the traction wire to the central axis is greater than a distance from the one end of the traction wire to the central axis.

Preferably, a range of a ratio of a distance from the other end of the traction wire to a central axis to a distance from the one end of the traction wire to the central axis is greater than or equal to 3 and less than or equal to 10.

By means of the foregoing technical solution, the present invention has the following advantages as compared with the prior art:

1) More than two traction wires are provided to control a guidewire output portion, angles can be controlled in a plurality of directions, and bending at 360 degrees of the guidewire output portion can be implemented through the coordination of the plurality of traction wires.

2) A rotary casing is also arranged, so that the guidewire output portion can rotate 360 degrees about the central axis. The rotary casing is also rotatable relative to a handle. Therefore, when the rotary casing rotates, parts for bending control are not affected.

3) When the guidewire output portion bends to a specific angle and needs to be fastened, a displacement of an adjustment limit sleeve is controlled, so that the handle ferrule can contract inward to be fastened on a clamping portion, so that an operator's hand for controlling an angle can be freed.

4) A first flexible bend member and a second flexible bend member are provided, so that a bending process is smoother and gentler.

DETAILED DESCRIPTION OF THE PREFERRED EMBODIMENTS

The present invention is further described below in detail with reference to the accompanying drawings and specific embodiments.

EMBODIMENT

Figure 1:
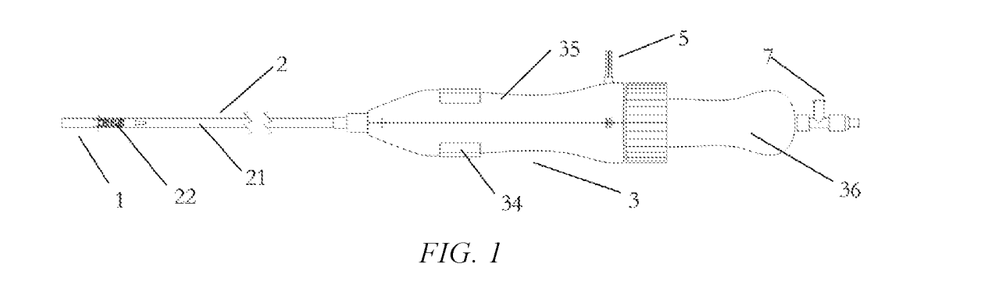
FIG. 1 is a schematic structural diagram according to an embodiment of the present invention.
Figure 2:
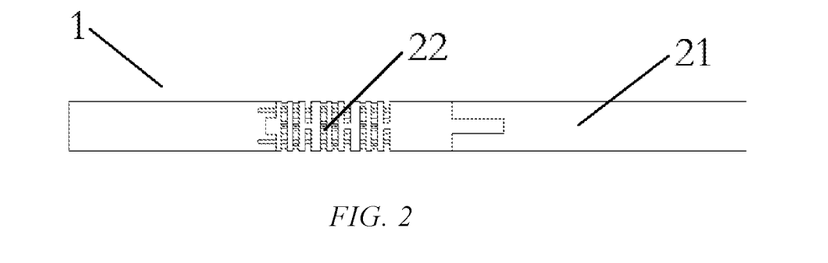
FIG. 2 is a schematic diagram showing a connecting structure between a guidewire output portion and a guidewire guide portion according to an embodiment of the present invention.
Figure 3:
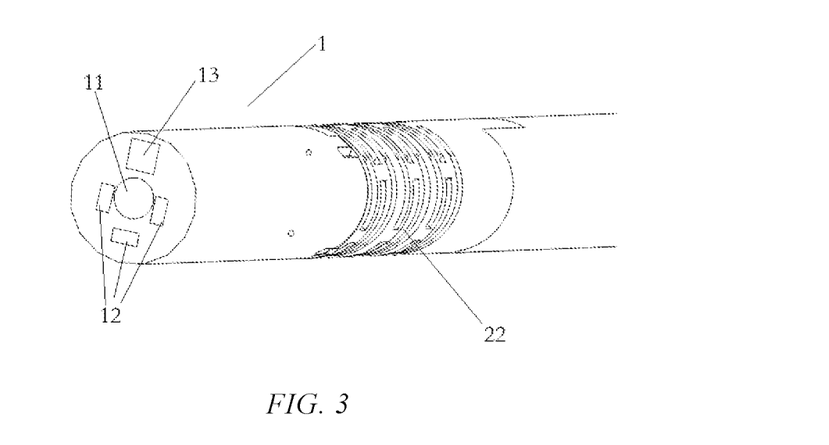
FIG. 3 is a partial enlarged view of a guidewire output portion according to an embodiment of the present invention.
Figure 4:
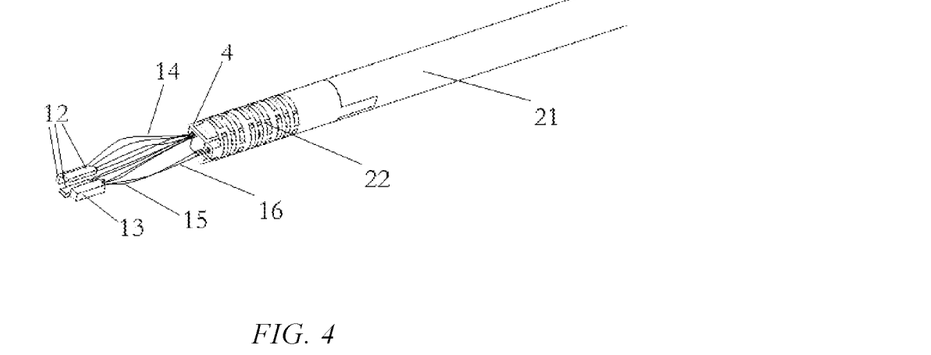
FIG. 4 is a schematic diagram of a guidewire output portion after a casing is removed according to an embodiment of the present invention.
Figure 5:
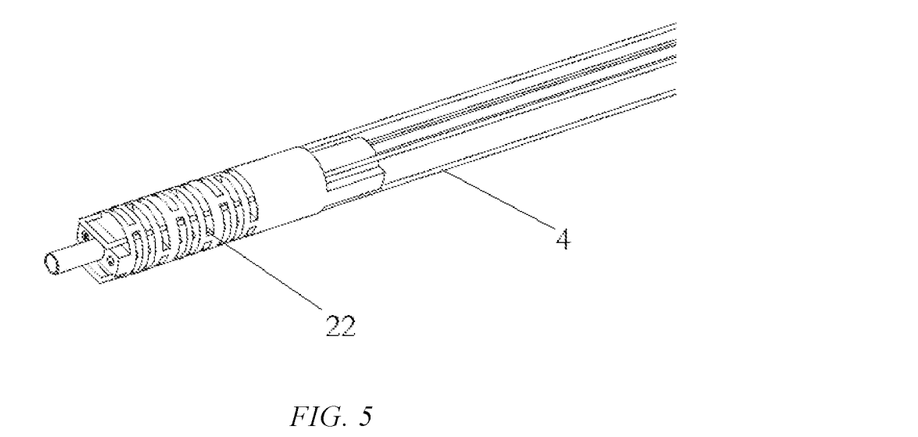
FIG. 5 is a schematic diagram showing a connecting structure of a traction wire at a distal end according to an embodiment of the present invention.
Figure 6:
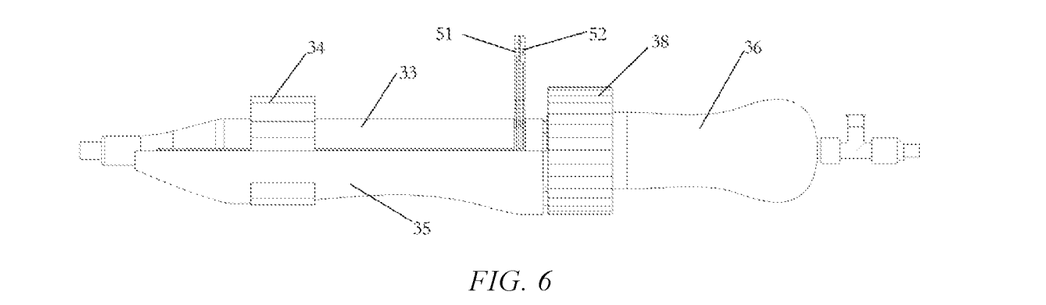
FIG. 6 is a schematic structural diagram of an adjustment control portion after a fastening casing is removed according to an embodiment of the present invention.
Figure 7:
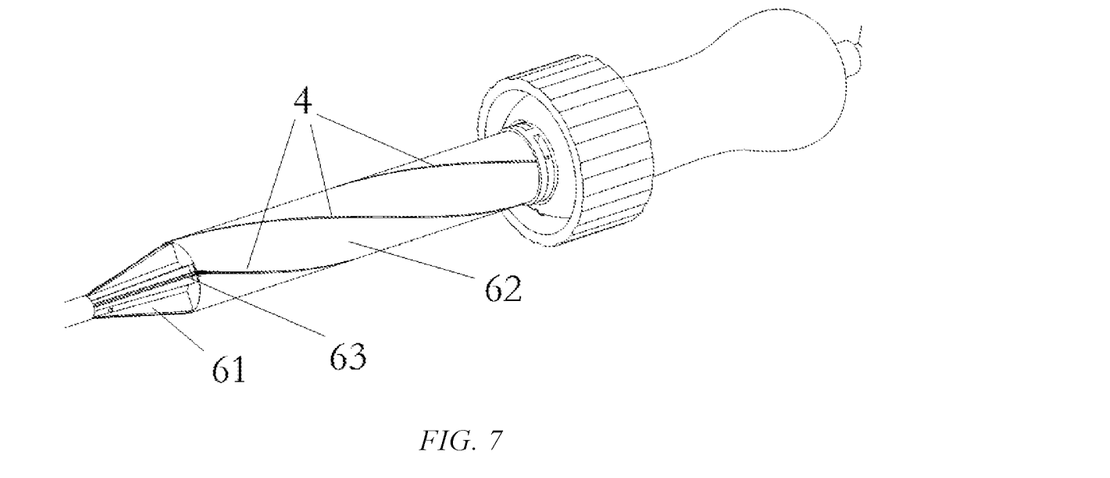
FIG. 7 is a schematic structural diagram of traction wires on an adjustment control portion according to an embodiment of the present invention.
Figure 8:
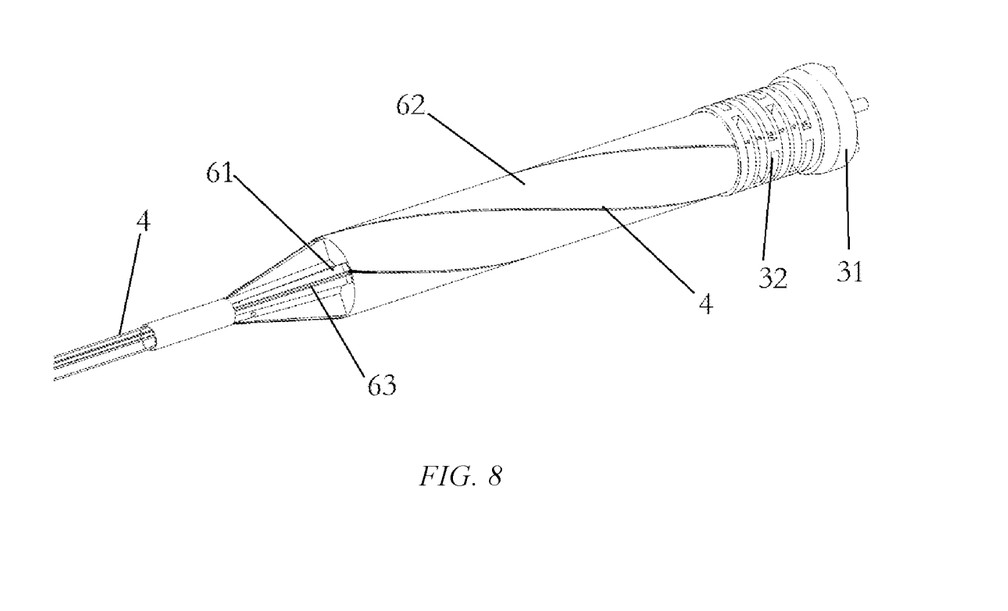
FIG. 8 is a schematic structural diagram of FIG. 7 after a handle is removed according to an embodiment of the present invention.
Figure 9:
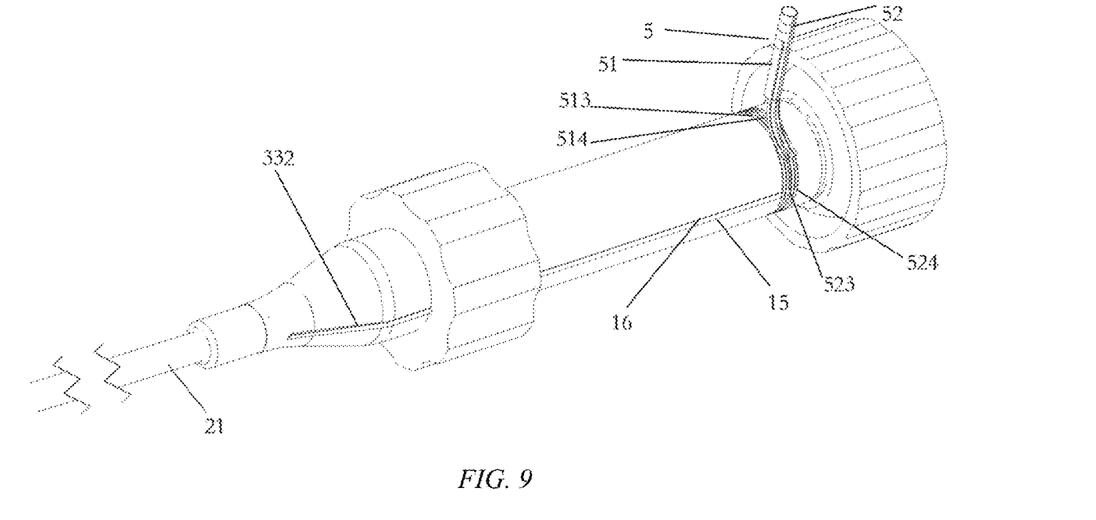
FIG. 9 is a schematic structural diagram of an input/output terminal on an adjustment control portion according to an embodiment of the present invention.
Figure 10:
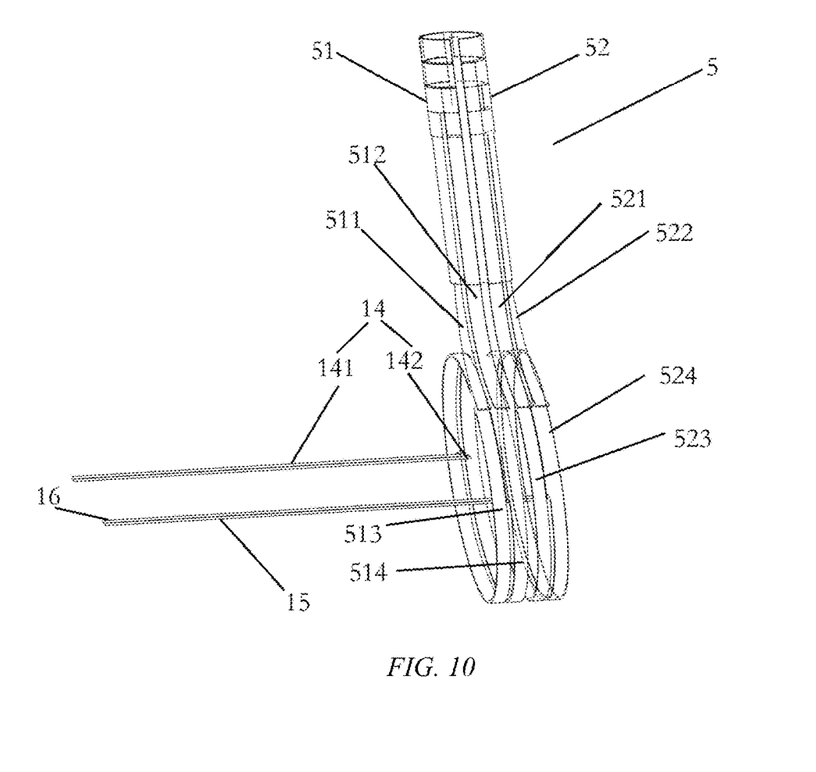
FIG. 10 is an enlarged view of an input/output terminal according to an embodiment of the present invention.
Figure 11:
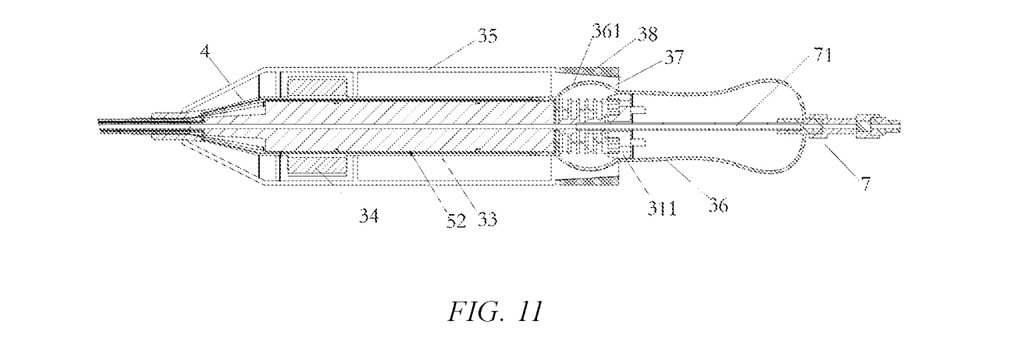
FIG. 11 is a sectional view of an adjustment control portion according to an embodiment of the present invention.

In this embodiment, a distal end is an end far away from an operator when the operator operates a instrument, and a proximal end is an end close to the operator when the operator operates the device. A central axis is approximately a central axis of a guide housing, but is also not limited to the axis. It may be understood that the central axis in this embodiment is a central axis about which a body part of the entire device is symmetrical. A guidewire described in this embodiment is a directing guidewire (or referred to as a guiding guidewire) commonly used in surgery. As shown in FIG. 1 to FIG. 11, this embodiment provides a medical instrument with angle adjustment device, and the positions and quantity of traction wires are set to enable a medical instrument having a distal end with an adjustable bending degree to adjust corresponding angles in a variety of directions as required, so that operations are flexible and convenient.

Details are described with reference to the embodiments. The medical instrument includes a guidewire output portion 1, a guidewire guide portion 2, an adjustment control portion 3, and traction wires 4. The guidewire output portion 1 is bendable relative to the guidewire guide portion 2. The guidewire output portion 1 is provided with a guidewire output hole 11. One end of each traction wire 4 is connected to a proximal end of the guidewire output portion 1, and the other end of the traction wire 4 is connected to a bending control member 31 of the adjustment control portion 3. The adjustment control portion 3 controls a bending angle of the guidewire output portion 1 through the traction wire 4. The quantity of the traction wires 4 is N. N is a positive integer and is greater than or equal to 3. In this embodiment, N is preferably 4. The ends of the N traction wires 4 are evenly distributed along the guidewire output portion 1.

The guidewire guide portion 2 includes a guide housing 21. A first flexible bend member 22 is provided at an end of the guide housing 21. An end of the first flexible bend member 22 is connected to the guidewire output portion 1.

Preferably, a traction through hole 211 for the traction wires 4 to pass through and a guidewire feeding through hole 213 for feeding a guidewire are provided inside the guide housing 21.

Preferably, the adjustment control portion 3 includes a rotary casing 33, the rotary casing 33 is provided with a channel for a guidewire to pass through, one end of the rotary casing 33 is fixedly connected to the guide housing 21, and the rotary casing 33 is externally connected to a rotary wheel 34.

Preferably, the other end of the rotary casing 33 is connected to the bending control member 31 by a second flexible bend member 32.

In addition, in this embodiment, the adjustment control portion 3 further includes a handle 36. A handle ferrule 361 is provided at an end of the handle 36. The handle ferrule 361 and a casing of the handle 36 are integrally formed. A clamping portion 311 of the bending control member 31 is disposed inside the handle ferrule 361. The adjustment control portion further includes a locking ring 38 and a limit sleeve 37. The limit sleeve 37 is sleeved on the handle ferrule 361. An inner surface of the limit sleeve 37 matches an outer surface of the handle ferrule 361. The locking ring 38 is sleeved on the limit sleeve 37. A conical inner surface of the locking ring 38 matches a conical outer surface of the limit sleeve 37. The handle ferrule 361 is made of an elastic material. The conical inner surface of the locking ring 38 matches the conical outer surface of the limit sleeve 37 by threaded connection.

Preferably, the guide housing 21 is symmetrically arranged about a central axis, and a distance from the other end of the traction wire 4 to the central axis is greater than a distance from the one end of the traction wire 4 to the central axis.

In addition, in this embodiment, a range of a ratio of a distance from the other end of the traction wire 4 to a central axis to a distance from the one end of the traction wire 4 to the central axis is greater than or equal to 3 and less than or equal to 10. In this embodiment, the ratio is preferably 5.

The application and functions of this application in a specific apparatus are further described below with reference to a specific design of an overall structure. A guidewire feeding device is described in this embodiment. A guidewire is specifically a surgical directing guidewire. The device in this embodiment is used in surgery to feed a corresponding directing guidewire into the human body, so that the directing guidewire passes through a narrow or occluded lesion in a coronary artery to a vascular distal end, to provide a path for pressurized expansion for feeding a balloon catheter or a stent to the narrow lesion.

Specifically, this embodiment includes the guidewire output portion 1, the guidewire guide portion 2, and the adjustment control portion 3 that are sequentially arranged from the distal end to the proximal end. The adjustment control portion 3 is used for controlling the direction of the guidewire output portion 1, and is specifically used for controlling rotation of the guidewire output portion 1 in an axial direction and bending of the guidewire output portion 1 relative to the guidewire guide portion 2. A surgical directing guidewire passes through a guidewire input portion 7 to enter the instrument in this application, and is eventually outputted from the guidewire output hole 11 in the guidewire output portion 1 after moving through the adjustment control portion 3 and the guidewire guide portion 2, to enter a body duct to implement a directing function.

The principle of bending is as follows: One end of the traction wire 4 is connected to the proximal end of the guidewire output portion 1, and the other end of the traction wire 4 is connected to the bending control member 31 of the adjustment control portion 3. The guidewire guide portion 2 includes the guide housing 21. Here, to facilitate description, the central axis of the guide housing 21 is used as the central axis of the entire guidewire feeding device.

To facilitate bending of the guidewire output portion 1 relative to the guidewire guide portion 2, the first flexible bend member 22 is provided at one end of the guide housing 21. An end of the first flexible bend member 22 is connected to the guidewire output portion 1. An end of the bending control member 31 is connected to the second flexible bend member 32. The first flexible bend member 22 and the second flexible bend member 32 are both made of a polymer elastic material and have hollowed-out structures. The bending of the bending control member 31 is controlled, so that the traction wires 4 are driven to pull the guidewire output portion 1 at the distal end. Due to distance differences generated in a plurality of traction wires 4, the guidewire output portion 1 is correspondingly bent.

In this embodiment, preferably a distance from a contact point between the traction wire 4 and the guidewire output portion 1 to the central axis is less than a distance from a contact point between the traction wire 4 and the bending control member 31 to the central axis.

By means of such an arrangement, a distance from a distal end of the traction wire, that is, one end connected to the guidewire output portion of the traction wire, to the central axis is less than a distance from the other end of the traction wire to the central axis on the adjustment control portion. When the bending control member of the control portion bends a first angle, the traction wires are driven to move a first distance. Correspondingly, an end, at the guidewire output portion, of the traction wire also moves the first distance. Because the one end of the traction wire is close to the central axis, the guidewire output portion bends a second angle. The second angle is greater than the first angle.

To implement that the distance from the contact point between the traction wire 4 and the guidewire output portion 1 to the central axis is less than the distance from the contact point between the traction wire 4 and the bending control member 31 to the central axis, specifically, in this embodiment, a traction wire guide member 6 is provided on the other end of the guide housing 21. The traction wire guide member 6 includes an expansion portion 61 and a horizontal portion 62 arranged from the distal end to the proximal end. The traction wires 4 pass through the guide housing 21 and are arranged along outer surfaces of the expansion portion 61 and the horizontal portion 62.

The expansion portion 61 has a conical surface. The horizontal portion 62 has a cylindrical side surface. The largest outer diameter of the conical surface is equal to an outer diameter of the cylindrical side surface. The expansion portion 61 is provided with a traction wire guide groove 63 which matches the traction wires 4, to guide directions of the traction wires 4 more accurately without causing a misplacement problem of the traction wires 4.

Preferably, the guidewire output portion 1 in this embodiment can further rotate along the central axis. In this embodiment, a specific implementation is as follows: The adjustment control portion 3 includes a rotary casing 33. The rotary casing 33 is provided with a channel for a guidewire to pass through. An end of the rotary casing 33 is fixedly connected to the guide housing 21. The rotary casing 33 is externally connected to a rotary wheel 34. The traction wire guide member 6 is arranged inside the rotary casing 33 and is fixedly connected to the rotary casing 33. An operator uses the rotary wheel 34 to drive the rotary casing 33 to rotate, to further drive the guide housing 21 until the guidewire output portion 1 rotates about the central axis, so that the guidewire output portion 1 at the distal end of the instrument in this embodiment can perform adjustment in a bending direction and can further implement rotary adjustment, thereby making the adjustment diversified and satisfying more requirements of the operator.

An angle change from one end to the other end of the traction wire 4 is a first angle α. Optionally, the first angle is in a range from 170° to 190°, so that an angle of the traction wire 4 is kept as close as possible to 180°, preferably 180°. That is, a connecting wire between one end and the other end of the traction wire 4 intersects the central axis. In this way, when the handle bends downward, the bending control member 31 of the adjustment control portion 3 may bend downward, to drive traction wires 4 located at an upper side to stretch. Correspondingly, traction wires at a lower side of the guidewire output portion 1, that is, the corresponding traction wire at the upper side of the adjustment control portion 3 is pulled toward the proximal end, to drive the guidewire output portion 1 to synchronously bend downward. When the handle bends upward, the guidewire output portion 1 also bends upward synchronously.

Specifically, a baseline is used to more clearly define angle changes of the foregoing the traction wire. A ray with one end of the traction wire 4 as a start point and perpendicular to the central axis is a first ray, a straight line with the other end of the traction wire 4 as a start point and perpendicular to the central axis is a second ray, and an angle between the first ray and the second ray corresponding to each traction wire 4 is 180°. That is, an angle change around the central axis from one end to the other end of the traction wire is 180°, which is more ergonomic. When a control part for controlling bending on the adjustment control portion 3 bends in one direction to pull the traction wires 4, one end of the traction wire 4 corresponding to an end portion of the guidewire output portion 1 and the other end of the traction wire corresponding to the adjustment control portion 3 are located at two sides of the central axis. Therefore, when the traction wires 4 is pulled in a direction, control parts for controlling bending on the guidewire output portion 1 and the adjustment control portion 3 bend in the same direction, which is more ergonomic.

The guidewire output hole 11, at least one lighting device 12, and at least one image acquisition device 13 are provided on the distal end of the guidewire output portion 1. The lighting device 12 and the image acquisition device 13 are disposed on an end surface of the distal end of the guidewire output portion 1, so that there is sufficient light for observation inside during surgery, and images inside can be continuously observed, and the device has a small spatial structure.

The lighting device 12 and the image acquisition device 13 are both connected to a power cable 14. The power cable 14 is used for providing electrical energy from an external power supply to the lighting device 12 and the image acquisition device 13. The image acquisition device 13 is further connected to a data transmission cable 15. The data transmission cable 15 is used for being connected to an external display unit or a data collection unit, and is used for transmitting an image signal acquired by the image acquisition device. In this embodiment, the lighting device 12 is specifically an LED lamp. There are specifically three lighting devices 12 and one image acquisition device 13. The four components are evenly distributed. That is, the four components are arranged at 90 degrees from each other.

To coordinate with the foregoing arrangement, a traction through hole for the traction wires 4 to pass through, an electric wire through hole, and a guidewire feeding through hole are provided inside the guide housing 21. There may be one or more traction through holes, one or more electric wire through holes, and one or more guidewire feeding through holes. Two of the traction through hole, the electric wire through hole, and the guidewire feeding through hole or all the three may share one cavity, or the three may be arranged separately.

The lighting device 12 and the image acquisition device 13 are respectively electrically connected to an input/output terminal 5 by the power cable 14 and the data transmission cable 15. The lighting device is preferably an LED lamp. The image acquisition device may be a miniature camera. Specifically, the input/output terminal 5 includes an energy supply terminal 51 and an image data transmission terminal 52. The energy supply terminal 51 is connected to a first conductive sheet group. The image data transmission terminal 52 is connected to a second conductive sheet group. The first conductive sheet group is in contact with a first conductive coil group. When the first conductive coil group rotates, the first conductive sheet group remains in contact with the first conductive coil group by using a biasing force generated from its own elastic deformation. The conductive coil group is arranged to be externally connected to the energy supply terminal by the conductive sheet groups, and the conductive sheet groups remain in contact with the corresponding conductive coil group by using a biasing force generated from their own elastic deformation, so that conductive coil group and a corresponding lead may rotate together with the guidewire output portion, and the position of the input/output terminal is kept unchanged, to facilitate connection to an external device.

The second conductive sheet group is in contact with a second conductive coil group. When the second conductive coil group rotates, the second conductive sheet group remains in contact with the second conductive coil group by using a biasing force generated from its own elastic deformation. The energy supply terminal 51 and the image data transmission terminal 52 are both fixedly connected to a fastening casing 35.

A plurality of conductive coil groups are arranged and are externally connected to the energy supply terminal by the conductive sheet groups, so that the conductive coil groups and corresponding leads may rotate together with the guidewire output portion, whereas the position of the input/output terminal is kept unchanged, to facilitate connection to an external device.

The first conductive sheet group includes a neutral wire conductive sheet 511 and a live wire conductive sheet 512. The first conductive coil group includes a neutral wire lead coil 513 and a live wire conductive coil 514 that are respectively correspondingly connected to the neutral wire conductive sheet 511 and the live wire conductive sheet 512. The power cable 14 includes a power supply neutral wire 141 and a power supply live wire 142. The power supply neutral wire 141 and the power supply live wire 142 are respectively correspondingly electrically connected to the neutral wire lead coil 513 and the live wire conductive coil 514.

One power supply neutral wire 141 and one power supply live wire 142 may be connected to the neutral wire lead coil 513 and the live wire conductive coil 514. A plurality of power supply live wires 142 and a plurality of power supply neutral wires 141 are respectively connected to the lighting device 12 and the image acquisition device 13 to provide power supply as an energy source. In other embodiments, ends of a plurality of power supply neutral wires 141 are connected to the neutral wire lead coils 513, and other ends are respectively electrically connected to a plurality of lighting devices 12 and the image acquisition device 13. Ends of a plurality of power supply live wires 142 are correspondingly electrically connected to the live wire conductive coil 514, and other ends are respectively electrically connected to the plurality of lighting devices 12 and the image acquisition device 13. The second conductive coil group includes an image signal transmission coil 523. The image signal transmission coil 523 is electrically connected to the data transmission cable 15.

The second conductive sheet group is provided with an image signal transmission sheet 521. The second conductive coil group includes the image signal transmission coil 523. The image signal transmission sheet 521 is correspondingly connected to the image signal transmission coil 523. The image signal transmission coil 523 is electrically connected to the data transmission cable 15.

The second conductive sheet group is provided with a control signal sheet 522. The second conductive coil group further includes an image control signal transmission coil 524. The control signal sheet 522 is correspondingly electrically connected to the image control signal transmission coil 524. The image acquisition device 13 is further electrically connected to an image control wire 16. The image control wire 16 is at the same time electrically connected to the image control signal transmission coil 524. The image control wire 16 is used for transmitting a control signal to the image acquisition device 13. The control signal is used for controlling a photographing angle and/or a photographing focal length of the image acquisition device 13.

The first conductive sheet group, the first conductive coil group, the second conductive sheet group, and the second conductive coil group are all made of conductive metal materials or conductive alloy materials. Further, the materials of the first conductive sheet group and the second conductive sheet group are both elastic metal materials, for example, elastic iron sheets or copper sheets. The power cable 14, the data transmission cable 15, and the image control wire 16 are common electric signal transmission leads in the prior art. The power cable is the most common lead for transmitting electrical energy. The data transmission cable and the image control wire may use common data cables to transmit data and instructions by electric signals.

In other alternative embodiments, the data transmission cable 15 may also be electrically connected to a wireless transmission device. The wireless transmission device is communicatively connected to the display unit, so that an acquired image signal can be directly sent to a data reception unit or a display unit communicatively connected to the wireless transmission device.

An object of arranging the conductive coil groups lies in that when circuits such as a power cable and a data transmission cable are arranged inside, in the instrument of this application, when the housing rotates along the central axis for adjustment, the power cable and the data transmission cable may rotate together. However, the input/output terminal 5 needs to be electrically connected to some fastening devices such as a power supply and a display unit. Therefore, the input/output terminal 5 is preferably an arrangement that implements this objective but does not rotate along with the remaining rotary adjustment assemblies, that is, a conductive coil group.

Specifically, the adjustment control portion 3 includes a rotary casing 33. The rotary casing 33 has a hollow structure, and is provided with a channel for a guidewire to pass through. The rotary casing 33 is fixedly connected to the guide housing 21. The guide housing 21 and the rotary casing 33 are both provided with space for accommodating the power cable 14 and the data transmission cable 15. Specifically, the space is an accommodating cavity or a concave groove. In this embodiment, the guide housing 21 is provided with two circuit accommodating cavities for separately accommodating the data transmission cable 15 and the power cable 14. The surface of the rotary casing 33 is provided with a circuit concave groove 331 for accommodating the data transmission cable 15 and the power cable 14. Two circuit communication grooves 332 are further separately provided on two sides of the rotary casing 33, so that the data transmission cable 15 and the image control wire 16 pass through the circuit communication groove 332 on one side to pass through the rotary casing 33 to enter the circuit accommodating cavities. The power supply neutral wire 141 and the power supply live wire 142 of the power cable 14 may pass through the circuit communication groove 332 on the other side to pass through the rotary casing 33 to enter the circuit accommodating cavities. A first conductive coil group 512 and a second conductive coil group 522 are provided between the rotary casing 33 and the fastening casing 35. The first conductive coil group 512 and the second conductive coil group 522 are both fixedly connected to the rotary casing 33. The power cable 14 is electrically connected to the first conductive coil group 512. The data transmission cable 15 is electrically connected to the second conductive coil group 522. The first conductive coil group 512 is electrically connected to the energy supply terminal 51. The second conductive coil group is electrically connected to the image data transmission terminal 52.

The rotary casing 33 is externally connected to a rotary wheel 34 and is sleeved by the fastening casing 35 outside. The fastening casing 35 is provided with an opening for the rotary wheel 34 to pass through. The rotary casing 33 is rotatable relative to the fastening casing 35. The fastening casing 35 facilitates holding.

The adjustment control portion 3 further includes a handle 36. A handle ferrule 361 is provided at an end of the handle 36. The handle ferrule 361 and a casing of the handle 36 are integrally formed. The clamping portion 311 of the bending control member 31 is disposed inside the handle ferrule 361. The bending control member 31 and the handle ferrule 361 are rotatable relative to each other in a central axis direction.

The adjustment control portion further includes a locking ring 38 and a limit sleeve 37. The limit sleeve 37 is sleeved on the handle ferrule 361. An inner surface of the limit sleeve 37 matches an outer surface of the handle ferrule 361. The locking ring 38 is sleeved on the limit sleeve 37. A conical inner surface of the locking ring 38 matches a conical outer surface of the limit sleeve 37.

The limit sleeve 37 is made of an elastic material. The conical inner surface of the locking ring 38 matches the conical outer surface of the limit sleeve 37 by threaded connection.

With the foregoing arrangement, when the rotary wheel 34 is adjusted, the bending control member 31 and the handle ferrule 361 are rotatable relative to each other in the central axis direction. Therefore, the handle does not need to rotate together during rotary adjustment. During bending adjustment, because the clamping portion 311 of the bending control member 31 is disposed inside the handle ferrule 361, the handle may drive the clamping portion 311 of the bending control member 31 to bend together relative to the central axis direction, so as to drive the guidewire output portion 1 to bend. The handle 36 is rotatable coaxially with the clamping portion 311, and the handle 36 and the clamping portion 311 are relatively fastened in an axial direction. The handle 36 therefore does not fall off from a clamping head 311, and is integrally formed with the casing of the handle 36 and indirectly fixedly connected to the clamping portion 311. The limit sleeve 37 is sleeved over the handle ferrule 361. When the limit sleeve 37 contracts inward, a relatively large frictional force is generated between the limit sleeve 37 and the handle ferrule 361. Therefore, the handle ferrule 361 may be fastened at an angle. That is, when the bending control member 31 drives the second flexible bend member 32 to rotate to an angle, the contraction of the limit sleeve 37 is controlled to fix a bending angle of the bending control member 31, thereby fixing the bending angle of the guidewire output portion 1 at the distal end.

The contraction of the limit sleeve 37 is controlled by using a limit ring sleeved on the limit sleeve 37. The locking ring 38 is sleeved on the limit sleeve 37, a conical inner surface of the locking ring 38 matches the conical outer surface of the limit sleeve 37, and the conical inner surface and the conical outer surface are threadedly connected, so that when the locking ring 38 is rotated and contracted, the locking ring 38 moves in the axial direction relative to the limit sleeve. Therefore, through the conical fit, the limit sleeve 37 contracts inward or restores and expands according to its own elastic restoration force.

The handle ferrule 361 is made of an elastic material. An outer surface of the handle ferrule 361 and the inner surface of an adjustment limit sleeve 37 fit in shape. When the adjustment limit sleeve 37 moves toward the proximal end, the handle ferrule 361 is pressed to contract inwardly. Optionally, the handle ferrule 361 has a conical outer surface, and the adjustment limit sleeve 37 has a conical inner surface. When the handle ferrule 361 and the adjustment limit sleeve 37 move relative to each other, the conical inner surface of the adjustment limit sleeve 37 presses the conical outer surface of the handle ferrule 361 to generate deformation in the conical outer surface of the handle ferrule 361, so that the handle 36 is fastened relative to the clamping head 311, to further fix the direction of the guidewire output portion 1 at an angle.

In this embodiment, a distance from the outer surface of the handle ferrule 361 to the central axis increases and then decreases from the proximal end to the distal end. A shape of the inner surface of the adjustment limit sleeve 37 matches a shape of the outer surface of the handle ferrule 361. Therefore, when the handle ferrule 361 moves toward the distal end, the outer surface of the handle ferrule is further compressed. Preferentially, the outer surface of the handle ferrule 361 matches the inner surface of the adjustment limit sleeve 37 by threaded connection.

The foregoing provides description completely according to the objective of the present invention. However, the present invention is not limited to the foregoing embodiments and implementations, and features in the embodiments may be combined with each other without causing any conflict. A person skilled in the art may make different changes and implementations within the scope allowed by the technical concept of the present invention.

What is claimed is:

1. A medical instrument with angle adjustment device, comprising a guidewire output portion (1), a guidewire guide portion (2), an adjustment control portion (3), and traction wires (4), wherein the guidewire output portion (1) is bendable relative to the guidewire guide portion (2), the guidewire output portion (1) is provided with a guidewire output hole (11), a first end of each traction wire (4) is connected to a proximal end of the guidewire output portion (1), a second end of the traction wire (4) is connected to a bending control member (31) of the adjustment control portion (3), the adjustment control portion (3) controls a bending angle of the guidewire output portion (1) through the traction wire (4), the number of the traction wires (4) is N, N is a positive integer and is greater than or equal to 3, and the ends of the N traction wires (4) are evenly distributed along the guidewire output portion (1), wherein the adjustment control portion (3) further comprises a handle (36), a handle ferrule (361) is provided at an end of the handle (36), the handle ferrule (361) and a casing of the handle (36) are integrally formed, and a clamping portion (311) of the bending control member (31) is disposed inside the handle ferrule (361), and wherein the adjustment control portion further comprises a locking ring (38) and a limit sleeve (37), the limit sleeve (37) is sleeved on the handle ferrule (361), an inner surface of the limit sleeve (37) matches an outer surface of the handle ferrule (361), the locking ring (38) is sleeved on the limit sleeve (37), and a conical inner surface of the locking ring (38) matches a conical outer surface of the limit sleeve (37).

2. The medical instrument with angle adjustment device according to claim 1, wherein the guidewire guide portion (2) comprises a guide housing (21), a first flexible bend member (22) is provided at an end of the guide housing (21), and an end of the first flexible bend member (22) is connected to the guidewire output portion (1).

3. The medical instrument with angle adjustment device according to claim 2, wherein a traction through hole (211) for the traction wires (4) to pass through and a guidewire feeding through hole (213) for feeding a guidewire are provided inside the guide housing (21).

4. The medical instrument with angle adjustment device according to claim 2, wherein the adjustment control portion (3) comprises a rotary casing (33), the rotary casing (33) is provided with a channel for a guidewire to pass through, one end of the rotary casing (33) is fixedly connected to the guide housing (21), and the rotary casing (33) is externally connected to a rotary wheel (34).

5. The medical instrument with angle adjustment device according to claim 4, wherein the other end of the rotary casing (33) is connected to the bending control member (31) by a second flexible bend member (32).

6. The medical instrument with angle adjustment device according to claim 1, wherein the handle ferrule (361) is made of an elastic material, and the conical inner surface of the locking ring (38) matches the conical outer surface of the limit sleeve (37) by threaded connection.

7. The medical instrument with angle adjustment device according to claim 1, wherein the guide housing (21) is symmetrically arranged about a central axis, and a distance from the second end of the traction wire (4) to the central axis is greater than a distance from the first end of the traction wire (4) to the central axis.

8. The medical instrument with angle adjustment device according to claim 1, wherein a range of a ratio of a distance from the other end of the traction wire (4) to a central axis to a distance from the one end of the traction wire (4) to the central axis is greater than or equal to 3 and less than or equal to 10.

* * * * *